United States Patent [19]

Sanderson et al.

[11] 4,372,921

[45] Feb. 8, 1983

[54] STERILIZED STORAGE CONTAINER

[76] Inventors: Roger S. Sanderson, 24772 Santa Clara, Dana Point, Calif. 92629; Robert C. Whelchel, 546 Tustin Ave., Newport Beach, Calif. 92660

[21] Appl. No.: 328,701

[22] Filed: Dec. 8, 1981

Related U.S. Application Data

[63] Continuation of Ser. No. 115,678, Jan. 28, 1980, abandoned, and a continuation-in-part of Ser. No. 895,239, Apr. 10, 1978, Pat. No. 4,247,517, which is a continuation-in-part of Ser. No. 821,042, Aug. 1, 1977, Pat. No. 4,251,842, which is a continuation-in-part of Ser. No. 734,228, Oct. 20, 1976, abandoned, which is a continuation-in-part of Ser. No. 703,044, Jul. 6, 1976, Pat. No. 4,196,160, which is a continuation-in-part of Ser. No. 640,824, Dec. 15, 1975, abandoned.

[51] Int. Cl.$^3$ .................... A61L 2/06; A61L 2/26; B65D 51/16; B65D 53/00
[52] U.S. Cl. .................... 422/300; 206/524.8; 220/231; 220/367; 220/371; 220/378; 422/293; 422/296; 422/297
[58] Field of Search ........... 422/26, 293, 296, 297, 422/300, 302, 33, 40; 220/72, 231, 367, 378, 357, 358, 371, 372; 206/524.8; 426/401, 403, 407

[56] References Cited

U.S. PATENT DOCUMENTS

| | | | |
|---|---|---|---|
| 2,092,445 | 9/1937 | Doulgeridis . | |
| 2,187,154 | 1/1940 | Ingersoll et al. | 220/358 |
| 2,997,397 | 8/1961 | Doulgheridis . | |
| 3,112,045 | 11/1963 | Chapman | 220/231 |
| 3,307,739 | 3/1967 | Cloyd et al. | 206/508 |
| 3,458,275 | 7/1969 | Bense et al. | 422/26 |
| 3,468,471 | 9/1969 | Linder . | |
| 4,105,407 | 8/1978 | Sanderson et al. | 422/26 |
| 4,149,650 | 4/1979 | Whelchel et al. | 220/378 |
| 4,196,166 | 4/1980 | Sanderson et al. | 422/300 |

FOREIGN PATENT DOCUMENTS 1642161  8/1980  Fed. Rep. of Germany .
1074275  7/1967  United Kingdom .

*Primary Examiner*—Bradley Garris
*Attorney, Agent, or Firm*—Knobbe, Martens, Olson, Hubbard & Bear

[57] ABSTRACT

A container lid (12) is held open by a support plate (18) carrying a chamber (20) which expands at a predetermined point in a sterilizing cycle to react against the lid, moving the plate outwardly to permit the lid to drop onto the container base. A resilient gasket (16) prevents fluid flow into the container after the lid is fallen, but permits fluid flow outwardly past the gasket when interior pressure exceeds exterior pressure. When the container is to be opened, a relief valve (60) relieves the vacuum within the container and filters air entering the container at that time.

9 Claims, 18 Drawing Figures

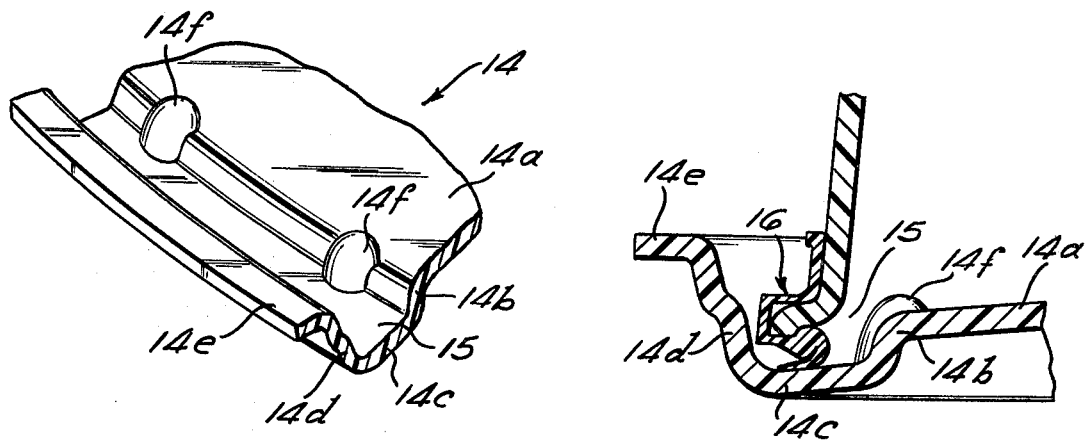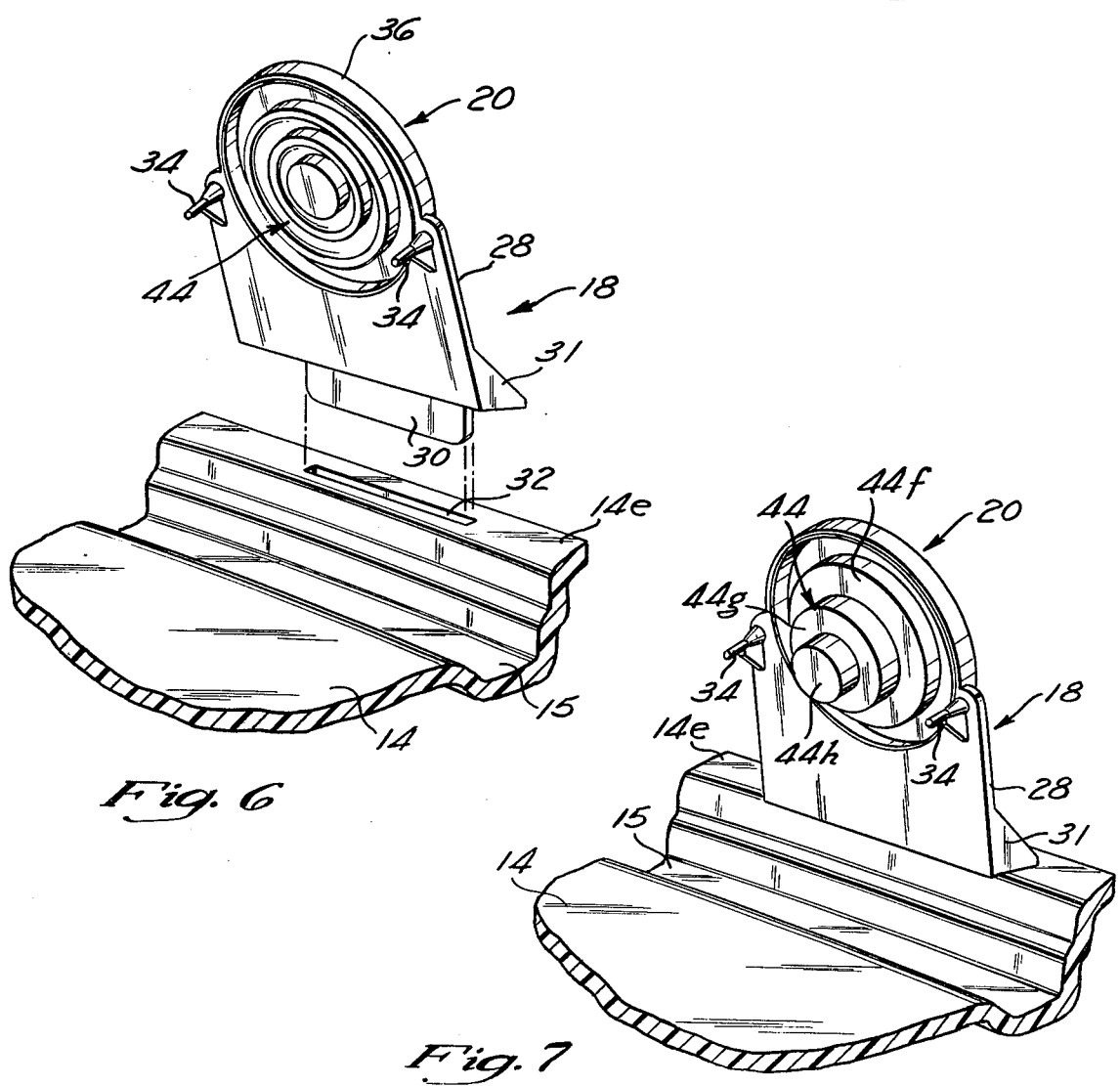

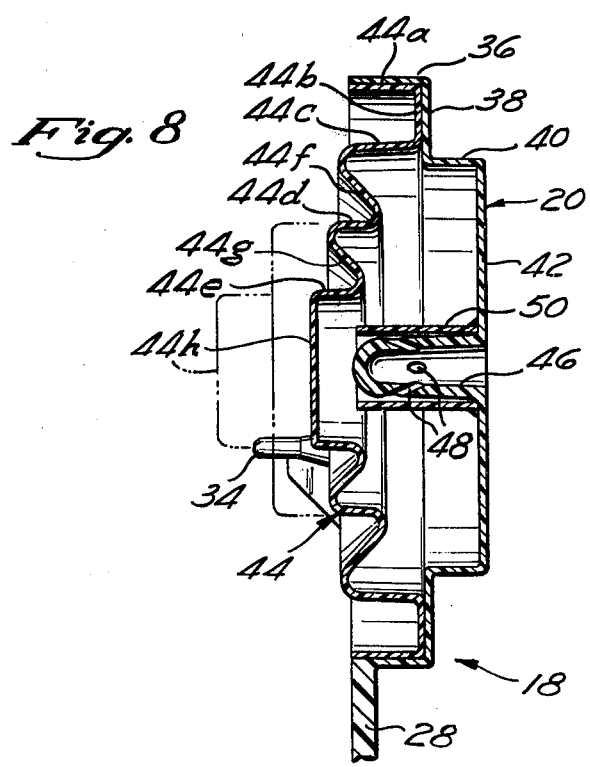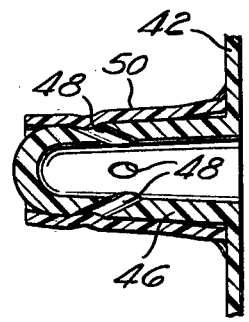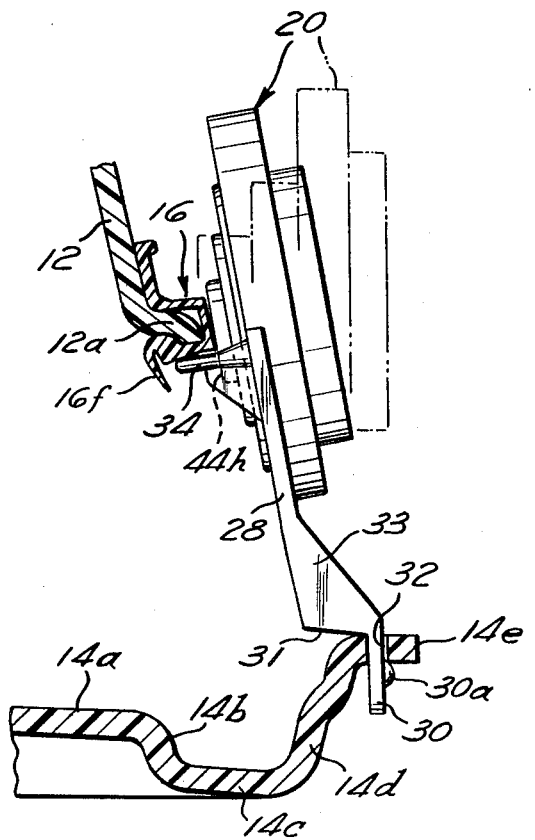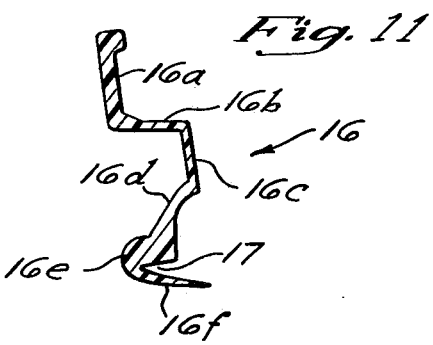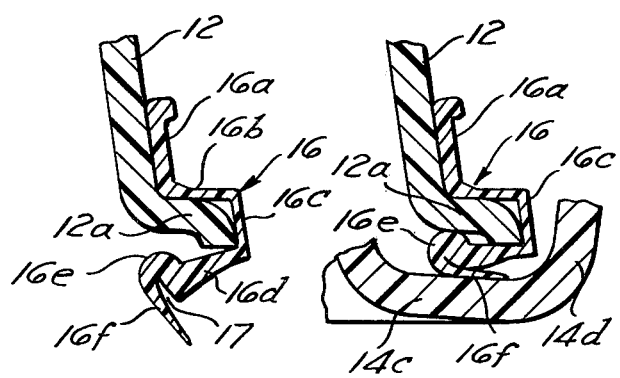

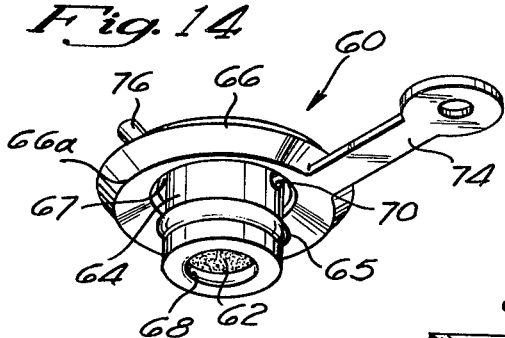
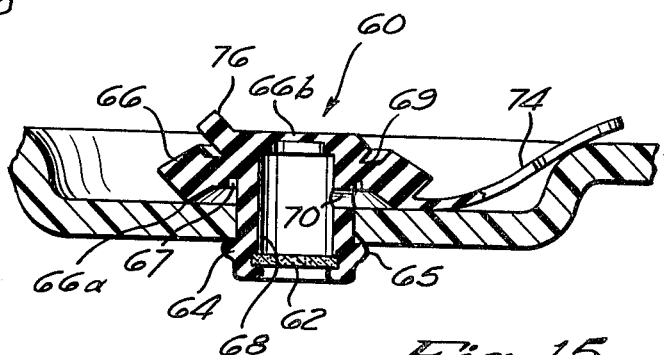
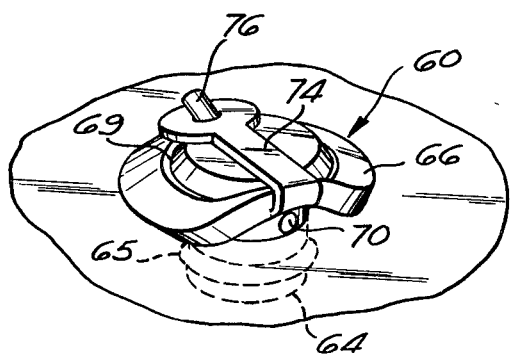
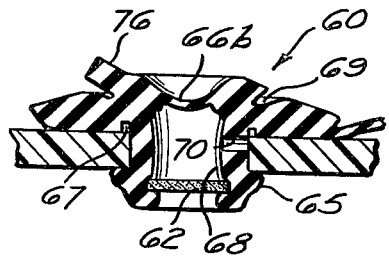
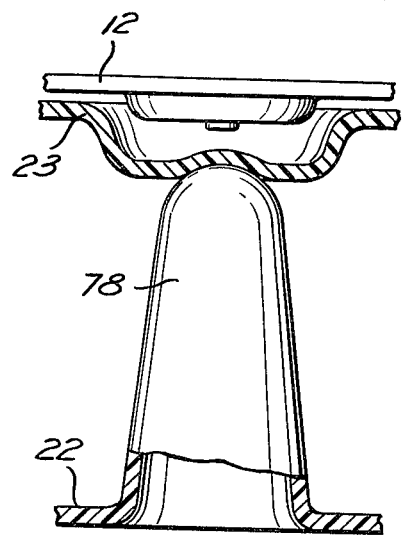

STERILIZED STORAGE CONTAINER

RELATED APPLICATIONS

This application is a continuation of application Ser. No. 115,678, filed Jan. 28, 1980 now abandoned.

This application is a continuation-in-part of U.S. patent application, Ser. No. 895,239, filed Apr. 10, 1978, which issued as U.S. Pat. No. 4,247,517 on Jan. 27, 1981 which is a continuation-in-part of U.S. patent application, Ser. No. 821,042, filed Aug. 1, 1977 which issued as U.S. Pat. No. 4,251,482 on Feb. 17, 1981, which is a continuation-in-part of U.S. patent application, Ser. No. 734,228, filed Oct. 20, 1976, which was abandoned in favor of continuation application, Ser. No. 923,359, filed July 10, 1978 which is now abandoned in favor of continuation application Ser. No. 144,068, filed Apr. 28, 1980, application 734,228 being a continuation-in-part of U.S. patent application, Ser. No. 703,044, filed July 6, 1976 which issued as U.S. Pat. No. 4,196,166 on Apr. 1, 1980, which is a continuation-in-part of U.S. application, Ser. No. 640,824, filed Dec. 15, 1975, which was abandoned in favor of continuation application, Ser. No. 827,992, filed Aug. 26, 1977 which issued as U.S. Pat. No. 4,149,650 on Apr. 17, 1979.

BACKGROUND OF THE INVENTION

This invention relates to an improved system for storing items while they are being sterilized, while they are being stored awaiting use, while they are in the process of being used, and after they have been used and are waiting resterilization. The invention particularly relates to a system having an improved actuator for automatically releasing a container lid at a predetermined temperature, an improved gasket for the container and an improved relief valve for the container. The system is particularly useful in connection with the sterilization and storage of medical items, such as surgical instruments.

As explained in the above-referenced patent applications, a need exists for an improved system for sterilizing surgical instruments and other medical items in that the common method of wrapping articles in sheets, sterilizing them and then storing them while still in the sheets, is an unsatisfactory approach. Scientific studies have shown that thirty percent of the packs prepared with sheets are contaminated by bacteria at the time of use. Further, instruments in such packs using sheets are contaminated with lint.

In the most recently filed patent application referred to above, articles to be sterilized are placed in a container, and the container is placed in an autoclave with the lid held open. After the articles have been sterilized, a pressure responsive actuator automatically releases the lid and allows it to fall into a closed position wherein a resilient gasket prevents further flow into the container. The actuator utilizes an expandable chamber which responds to pressure changes to produce an actuating movement. In a preferred approach, a quantity of sterilizing fluid is captured within the chamber by means of a temperature responsive valve. Although the systems disclosed in the earlier applications are valuable approaches, further improvements have been made in connection with a production version of the system.

SUMMARY OF THE INVENTION

A support plate is mounted on the periphery of a container base, and a projection or other support means on the support plate holds the lid in open position. A bellows or other suitable expandable chamber is mounted on the support plate; and at the end of the sterilizing phase of the autoclave cycle a chamber expands against the lid to force the support means away from the lid and allow it to fall onto the base. Advantageously, the support plate may be molded as a one-piece, relatively stiff plastic member, with means on its lower end for mounting on the periphery of the container base. In a preferred approach, the support plate has a pair of projections which extend beneath the edge of the lid to hold it in open position. A thin diaphragm in the form of a bellows construction is secured to the plate so that the diaphragm in combination with the plate uniquely forms the expandable chamber. Further, the support plate is provided with an inlet nipple that extends into the expandable chamber to permit steam or other sterilizing fluid to enter the chamber during the sterilizing phase of the autoclave cycle. A heat shrinkable sleeve valve element surrounds the nipple to close the chamber during the sterilizing phase to capture a volume of fluid in the chamber.

As the lid falls onto the base, it is critical that a seal be provided to prevent further flow into the container. A resilient gasket carried by the lid is formed with a lower flap having a feathered edge which engages a mating surface in the base to provide this initial seal. As a vacuum is formed in the container either by a final vacuum in an autoclave cycle or by the cooling of the residual environment in the container, the gasket is further compressed between the lid and the base. An enlarged bead on the gasket is compressed between the lid and the base to form a second seal for the container. Thus the container contents are sealed and preserved in a sterile, lint-free environment.

Because of the excellence of the seal obtained with the gasket, a vacuum is maintained in the container for an extended period of time. Consequently, to remove the lid of the container, it is necessary to release the vacuum. This is accomplished by providing a manually operated relief valve which plugs into a hole in the lid. During this operation, air rushes into the container. Since the lid is normally removed in an area which is not totally sterile, there is a potential source of contamination. To minimize this effect, the relief valve of the invention incorporates a small filter that removes dust and most other particles in the air. When the vacuum in the container is to be relieved, it is only necessary to pull on a tab attached to the valve flange to expose the valve opening and allow air to enter.

The container is constructed to withstand atmospheric pressure when a very high vacuum exists within the container. Nevertheless, with very large containers it is desirable to provide some additional supporting structure as a safety precaution. Thus, as another feature of the invention, an instrument basket positioned in the container is arranged to support the lid. Further, the basket may be provided with a cone-shaped projection extending upwardly from its bottom wall toward the container lid, or such projection may be formed on either a lid or the base and used with or without a basket. Thus, if the lid should commence to buckle due to the pressure, the support cone will distribute the load and limit the inward movement.

SUMMARY OF THE DRAWINGS

For a more thorough understanding of the invention, refer now to the following detailed description and drawings in which:

FIG. 4 is a fragmentary, perspective view of one end of the container base;

FIG. 5 is a fragmentary, cross-sectional view of the container base of FIG. 4 showing the lid and gasket positioned on the base, when the other end of the lid is held in an open position;

FIG. 6 is a perspective, exploded view of the expandable chamber actuator and a fragment of the container base illustrating the manner in which the actuator is mounted on the base;

FIG. 7 is a view like FIG. 6 but with the actuator mounted on the base and the chamber expanded;

FIG. 8 is a cross-sectional view of the expandable chamber showing the expanded position of the chamber in phantom lines;

FIG. 9 is a cross-sectional view of the inlet valve of the expandable chamber showing the valve in closed position;

FIG. 10 is a fragmentary view of the container showing the actuator in side elevation on the container base and holding the lid open showing the lid, base and gasket in cross-section;

FIG. 11 is a cross-sectional view of the gasket free form;

FIG. 12 is a cross-sectional view of the gasket mounted on a portion of the lid, also shown in cross-section;

FIG. 13 is a cross-sectional view of a portion of the lid, gasket and base with the lid in closed position on the base;

FIG. 14 is a perspective view of the relief valve for the sterilizing container;

FIG. 15 is a cross-sectional view of the valve of FIG. 14 installed in an opening in the container lid; and FIG. 15b shows the valve with a vacuum in the container;

FIG. 16 is a perspective view on the upper side of the valve of FIG. 14 showing the valve held in open position; and FIG. 17 is a side view partially sectionalized showing a support cone in the container basket illustrating the relation between the cone, basket cover, and the container lid.

DETAILED DESCRIPTION

Figure 1:
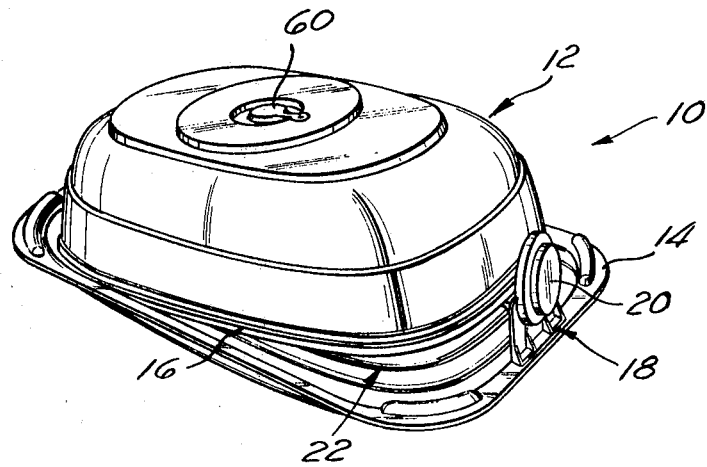
FIG. 1 is a perspective view of the overall container showing the lid of the container held in an open position.
Figure 2:
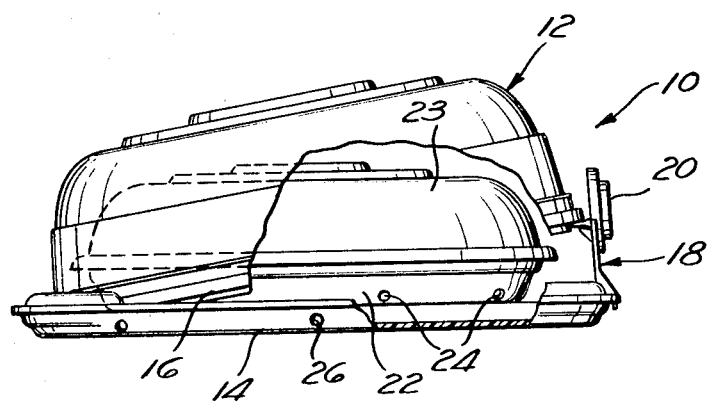
FIG. 2 is a side elevational view of the container of FIG. 1, partially cut away.

Referring now to FIGS. 1 and 2, there is shown a container 10 having access means or a lid 12 closing the open upper side of a base 14, with a gasket 16 carried by the lid and extending between the base and the lid. The container illustrated has a generally oval or racetrack configuration with the container lid having a somewhat dome-shape for strength purposes. Other configurations, such as circular, could also be employed. The upper portion of the lid is shaped to mate with recesses in the container base to facilitate stacking of the containers.

One end of the lid 12 is held open by an actuator 18 which is mounted on the base 14. The actuator includes a bellows-like inflatable chamber 20 which operates to release a lid at a desired point in an autoclave sterilizing cycle, allowing the lid to drop to the position shown in FIG. 3. FIG. 2 also shows a basket 22 and cover 23 within the container for holding items to be sterilized and to add support to the container when a vacuum exists in it. One suitable material for the container is polysulfone which is sold by Union Carbide Company.

The basket includes a plurality of holes 24 spaced around the lower side wall of the basket, to permit sterilizing fluid to circulate and to allow air to escape. Also provided are a plurality of drain holes (not shown) in the basket bottom wall to permit condensation to drain from the basket. Referring to FIG. 5 it may be seen that the container base 14 includes a bottom wall 14a which slopes downwardly and outwardly to a shoulder 14b leading to a peripheral groove 15. The bottom wall 14c of the groove 15 also slopes slightly downwardly in the outward direction to insure that condensation will flow through the drain holes in the basket and drain holes 26 in the base, shown in FIG. 2. The periphery of the base includes an upwardly and outwardly sloping wall 14d terminating in a generally horizontal flange 14e.

The base is formed with protuberances 14f to help guide the lid into its proper position when it is being installed, as shown in FIG. 1, and to help prevent the lid from being improperly positioned on the base. FIG. 5 shows the condition of the gasket, lid and base on the left end of the container when the right end of the container is held in open position as shown in FIG. 1.

Referring to FIGS. 6 and 7, it may be seen that the actuator 18 includes a plate-like member 28 having on its lower end a tab 30 which snaps into a slot 32 formed in the base flange 14e on the right end of the container as shown in FIG. 1. The actuator 18 further includes a pair of projections or posts 34 which extend outwardly from the plate 28. The plate 28 is preferably formed as a one-piece plastic member formed in a single molding operation.

Referring to FIG. 10, it may be seen that the tab 30 on the plate 28 includes one or more detents 30a which require the tab 30 to be snapped into position through the slot 32 in the flange 14e. This attachment coupled with the sides of the slot 32 in the somewhat horizontal wall 31 on the plate 28 support the actuator plate in a position extending upwardly approximately as shown in somewhat cantilever fashion. As can be seen the post-like projections 34 on the support plate 28 connect to the lid 12 by extending beneath the gasket 16 on the lid. Actually, with the lid removed but with the support plate mounted on the base as shown in FIG. 10, the upper end of the support plate will move further than shown in FIG. 10 towards the lid 12. This insures that the lid is securely supported when the container is placed in an autoclave. Note from FIG. 10 that the support plate 28 extends inwardly towards the lid at its upper end as opposed to being completely vertical.

The support plate 28 provides a number of different characteristics. First, it should be sufficiently stiff and strong to support the lid and to provide the necessary reliability. In addition it should be relatively inexpensive so that it may be disposable. Molding the support plate 28 in a single operation with its multiple functions greatly contributes to this. In order to minimize the amount of material required and yet attain the necessary stiffness and flexibility, the plate may be formed with a plurality of gussets 33 extending between the horizontal wall 31 and the approximately vertical portions of the plate. Similarly, the edges of the upright portion may be thickened or ribbed to provide the necessary strength.

Referring to FIG. 8 as well as to FIG. 6, it may be seen that the expandable chamber 20 is partially formed by a portion of the support plate 28. More specifically, the upper portion of the support plate is molded with a circular recess of two different diameters. The outer portion includes a cylindrical wall 36 and an annular wall 38, which is further connected to a smaller diameter cylindrical wall 40 which is joined to a circular end wall 42. Together these walls form a cup-shaped recess.

The expandable portion of the chamber 20 is formed by separate bellows-like element 44 molded of a plastic material similar to that from which the plate 28 is molded but being of thinner cross-section and being more flexible. As can be seen the diaphragm 44 includes an outer cylindrical wall 44a connected to an annular wall 44b which mate with the walls 36 and 38 on the plate 28. These walls are joined by suitable means to form the expandible chamber 20. The diaphragm 44 further includes short cylindrical wall sections 44c, 44d and 44e with consecutively smaller diameters joined by connecting wall sections 44f and 44g. A central circular wall section 44h connected to the cylindrical wall 44e forms an end wall of the chamber. As can be seen from the phantom lines in FIG. 8, the diaphragm 44 assumes the position indicated when the chamber is fully expanded. Note that the cylindrical walls maintain their approximate configuration but are moved outwardly due to the flexibility of the connecting annular wall sections 44f and 44g.

The support plate 28 includes a tubular portion or nipple 46 which is formed integral with the wall 42 and projects into the chamber 20. The inner end of the nipple is closed but a plurality of ports 48 in the side wall of the nipple connect the chamber 20 to the space around it. The nipple 46 tapers slightly inwardly to facilitate a single molding operation for the plate 28 and the ports 48 are formed at an angle to the side wall of the nipple so that the ports may also be made during the molding operation. That is, the mold structure forming the interior of the nipple and the ports may be withdrawn from the back side of the plate 28 at the completion of a molding operation. The material forming the plate is somewhat flexible to permit such.

Positioned loosely over the nipple 46 is a cylindrical sleeve 50 made of heat-shrinkable material. Although the sleeve is relatively confined within the chamber, it may be more positively secured to the plate 42 by a small amount of adhesive on the end of the sleeve.

Referring to FIG. 11, the gasket 16 provides a critical function requiring very flexible resilient material formed in a specific design. The gasket 16 includes an upper generally cylindrical portion 16a having on its upper edge a thickened bead adding to strength. The lower end of the portion 16a is connected to the upper leg 16b with a central section which takes a generally U-shape when installed on the lid. In addition to the leg 16b, this includes an annular wall 16c and a lower leg 16d, which in its free form shape extends somewhat downwardly. The outer end of the leg 16d is thickened to form a sealing bead 16e which leads to a thin flap 16f which tapers to a feathered lower edge. Note that there is a rather acute angle 17 between the flap 16f and the back side of the bead portion 16e.

As may be seen from FIG. 12, the gasket 16 mounts on an outwardly extending flange 12a formed on the lower end of the lid 12. The outer upper surface of the flange 12a is rounded as shown in FIG. 12 while the lower outer edge of the flange 12a is generally flat to mate with the gasket leg 16d when the lid is seated as shown in FIG. 13. The juncture between the flange 12a and the remainder of the lid 12 on the inner surface of the lid is smoothly rounded as can be seen from FIG. 12. Note also that the vertical thickness of the flange 12a is slightly greater than the wall thickness at the outer extremity of the flange. As seen from FIG. 12, positioning the gasket on the lid flange causes the gasket leg 16d to move upwardly somewhat so that the walls 16b, 16c and 16d move closer to a U-shape. The gasket assumes this configuration where ever it can hang free on the lid 12. In other words, referring to FIG. 1, the gasket would assume the position shown in FIG. 12 throughout its periphery except that the gasket on the left end of the container will appear approximately as shown in FIG. 5 and the gasket on the right end of the container in the area of the support actuator 18 will be as shown in FIG. 10.

OPERATION

When the container is first placed in the autoclave, the actuator will be in the position shown in FIGS. 1 and 10 holding the lid open and the expandable chamber 20 will be in the position shown in FIG. 8. If the particular autoclave cycle being used includes one or more preliminary vacuum phases to withdraw air from the containers, no movement of the actuator will occur, since the port 48 and the valve for the inflatable chamber 20 are open and not covered by the sleeve 50. Any pressure changes within the autoclave will be automatically applied to the interior of the chamber as well. When a high temperature sterilizing fluid such as gas or steam is applied to the autoclave, the fluid flows into the interior of the container and through the open lid into the interior of the basket through the ports 24, to displace the air and sterilize the container and the basket contents. Since the gasket 16 is positioned on the lid 12 relatively loosely, it has been found that the sterilizing fluid will also effectively sterilize the lower surfaces of the lid and the surfaces of the gasket.

The sterilizing environment applied to the container will of course also enter the chamber 20 through the ports 48. The elevated temperature of the fluid will cause the sleeve-like valve element 50 to shrink and cover the ports 48, as shown in FIG. 9. The high temperature, high pressure fluid is thus captured in the chamber. No change however occurs in the volume of the chamber during the remainder of the sterilizing phase, since temperature and pressure surrounding the chamber is essentially the same as that within it. Most autoclaves have some minor variations in temperatures and pressures during the sterilizing phase but such variations are not significant enough to cause the actuator to perform its actuating function. Thus, during the entire sterilizing phase, the lid of the container remains raised on one edge from the base such that fluid can flow freely into and out of the container. It is important that the lid be raised sufficiently to permit the sterilizing fluid to circulate freely and displace the air in the container. Preferably the lid should be raised at least a third of the height of a dome-shaped lid. It is also important that the circulation holes 24 in the basket be sized and spaced to permit the sterilizing fluid to displace the air in the basket. Condensation drains from the basket 22 through the holes in the bottom, and from the container through the drain holes 26 in the container base 14.

Figure 3:
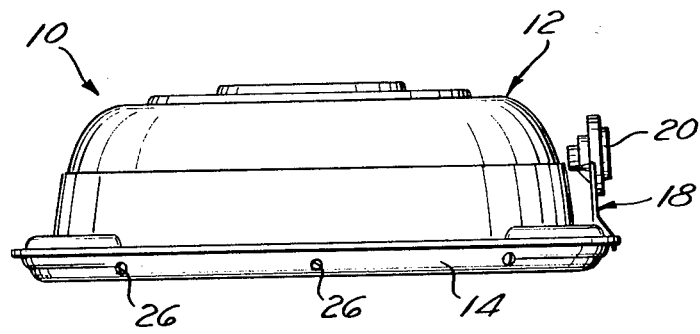
FIG. 3 is a side elevation of the container of FIG. 2 after the lid has fallen into closed position.

At the completion of the sterilizing phase of the cycle, there is an immediate pressure drop. Temperature also drops but this is much more slowly. As the pressure drops in the autoclave, the expandable chamber 20 expands due to the fact that the pressure of the steam captured within the chamber is greater than the pressure surrounding it. Thus, the bellows-like diaphragm 44 of the chamber 20 will move to the configuration shown in phantom lines in FIG. 8 and shown in solid lines in FIGS. 3 and 7. Since the central wall 44th of the diaphragm 44 is engaging the outer edge of the lid or its gasket, 16, as shown in FIG. 10, the actuator plate 28 is urged to pivot in a clockwise direction into the phantom line position shown in FIG. 10, this position also being shown in FIG. 3. The actuator moves because the resistance to movement provided by cantiliver mounting arrangement is much less than that of the lid 12. Thus, as the actuator moves, its projections or posts 34 are withdrawn from beneath the lid, allowing it to fall. Note from FIG. 8, that the wall 44h of the diaphragm 44 extends beyond the tip of the projections 34 when the bellows is fully expanded. This insures that the lid will be released. With the lid released, the actuator will move back slightly somewhat towards the upper portion of the container lid, as shown in FIG. 3, but this movement is somewhat limited while the expandable chamber is still expanded.

The lid falls into the proper position on the base and the gasket 16 assumes the approximate position shown in FIG. 13. The sloping wall 14d helps guide and lid into the peripheral groove 15 and the surfaces of the groove are smoothly curved to facilitate proper positioning of the lid. Correspondingly, the extremely flexible and resilient flap 16f on the gasket insures a proper seal on a reliable basis. In a gravity-type autoclave cycle wherein there is no final vacuum phase for withdrawing residual sterilizing environment from the autoclave, a vacuum is nevertheless formed within the container as the residual environment within the container cools and condenses, and as atmospheric pressure is introduced into the autoclave surrounding the container. The pressure differential between the interior and the exterior of the container may be quite small for a period of time in some situations such that it is important that a gasket prevent flow into the container at this time and the feathered edge of the gasket performs this function. At the same time, if the pressure within the container should be temporarily greater than the pressure on the outside of the container, the gasket feathered edge will readily permit flow out of the container, thus acting like a one-way valve. As the pressure on the interior of the container drops relative to the exterior atmosphere pressure, the lid is drawn more tightly against the base thus compressing the gasket more. This causes the bead 16e of the gasket to be further compressed between the lid and the base, becoming the primary seal for the container.

If the container is utilized in an autoclave providing a final vacuum phase, the residual environment in the autoclave is quickly withdrawn and the residual environment within the container is likewise withdrawn past the feathered edge of the gasket. When atmospheric pressure is introduced into the autoclave, the feathered edge of the gasket prevents flow into the container; and a quickly produced pressure differential between the interior and exterior of the container compresses the gasket greatly so that the bead 16e seals the container more tightly. Consequently, the container contents are sealed in essentially atmosphere free sterile environment, until the contents are to be used.

When the container is removed from the autoclave, the actuator 18 may be manually removed from the slot 32 in the container base and discarded. It is convenient to have a disposable type in a hospital environment, and the economics are such that this is a very practical approach. Alternatively, the actuator could be recycled by installing a new temperature responsive value in the expandable chamber, or by employing a value of a type that would recycle automatically. As one example the nipple 46 could be made as a separate component and be removably attached to the plate, and thus could be removed to permit replacement of the value element 50 and then reinstalled. Such an approach might be most practical, if sterilization of the container and their contents is to be performed by specialists at a central location.

The container and its contents are then transported to a storage area or to the point where the contents are needed. In use, the container is typically moved to the general area of use, but the lid of the container is actually removed somewhat remote from the actual operating or other use area in that the exterior of the container is contaminated during storage. When the lid is removed, the sterile basket on the interior protects the contents from falling dirt or other particles. The basket is carried to the actual area of use, and the cover on the basket is removed to provide access to the instruments or other items within the basket. This approach provides maximum sterility.

Relief Valve

Because of the high vacuum within the container, it is impossible to remove the container lid without relieving the vacuum. For this purpose, the relief valve 60 shown in FIGS. 1, 14, 15 and 16 is provided. As seen from FIG. 1, the relief valve is located in the top wall of the lid 12; however, it should be recognized that such a valve can be placed in other locations as well. Referring to FIG. 14, the valve is made of flexible resilient material as a one-piece member except for an inner filter 62. The valve includes a generally tubular projection or plug 64 which is open on its lower end and enclosed by an enlarged resilient flange 66 on its upper or outer end. A passage 68 through the projection 64 opens to a port 70 in a side wall of the projection immediately beneath the flange 66.

In use, the projection 64 is inserted through an opening in the lid 12. This operation is performed with the rigid, metal foam filter removed. The filter 62 is then installed in the lower end of the plug portion 64 as shown in FIG. 15. This not only secures the filter within the plug extending across the passage, but also helps pull the valve in a sealed condition in combination with a ring 65 on the exterior of the plug. The normal position of the valve when the container is not vacuumized is as shown in FIG. 15 with the annular edge 66a of the flange 66 against the outer surface of the lid thus preventing flow into the container through the port 70 and passage 68.

When the container lid 12 moves to its closed position, the valve 60 prevents air flow into the container; and as a vacuum is formed within the container, the exterior pressure forces most of the lower surface of the valve flange 66 against the lid. The annular relief groove 69 in the upper surface of the flange 66 and the annular groove 67 in the lower surface adjacent the plug 64 enable the flange to flatten readily. In addition, the thin upper wall 66b of the flange covering the end of the passage 68 is drawn inwardly because of the vacuum. This provides visible indication to an observer that a vacuum condition exists in a particular container.

When the vacuum is to be released to enable the container lid to be withdrawn, a tab 74 is manually pulled to lift the edge of the flange 66 away from the lid so that air may flow into the port 70 and through the passage 68 in the valve. If desired, the tab may be hooked on a tab holder 76 as shown in FIG. 16. This may be convenient in that the filter 60 is so fine that it will take several seconds for the pressure to equalize in a large container. All of the air entering the container must of course pass through the filter 62. Consequently, even though the entering air has not been subjected to high temperature sterilization, a high percentage of the dust, lint and other particles within the air are removed as the air passes through the filter. Once the container interior and exterior equalize, the lid can be lifted off of the base to provide access to the inner gasket.

Lid Support

Although the container 10 is constructed to withstand a high vacuum, it has been found desirable to provide further mechanical support for large containers. A preferred approach for providing such support is illustrated in FIG. 17. The basket cover 23, which is supported on its periphery by the basket base 22, is dimensioned so that its upper surface mates with the lower surface of the lid 12; and normally with a container lid tightly closed on a container base, the lid would be slightly spaced from the inner basket. However, if an overstressed condition should occur, such that the lid 12 should begin to buckle, it will engage the upper surface of the basket cover 23 to be supported thereby.

Further, with particularly large containers, the lower portion of the inner basket 22 is provided with an upwardly extending cone-shaped projection 78 that terminates near the cover 23 of the basket. The periphery of the basket cover 23 rests on the basket base 22, but it also engages or comes close to engaging the upper end of the support cone. The container lid 12 is formed with recesses that are complementarily receives in the basket cover. Thus in the overstressed situation the basket cover will reset upon the upper end of the support cone 78 on the basket base, thus preventing collapse of the lid. Of course, a suitable support may be provided as a separated element, or attached to either the container lid or base, and used without a basket; or used with a modified basket which would fit with a support.

The operation of two different autoclave cycles is briefly discussed above. It is believed that this is sufficient for purposes of understanding the invention. However, if further information is desired, reference may be had to the surface mentioned U.S. patent application Ser. No. 895,239 or Ser. No. 821,042, both of which discuss such cycles in greater details and include a time, temperature and pressure graph of such operations.

Although the container is primarily designed for use with a steam or gas autoclave sterilizing cycle, it should be understood that it is also very useful with other sterilizing techniques. With microwave sterilizing, the container lid may be positioned on the container base in a lightly closed condition. As the contents are heated, any pressure increase within the container may vent from the container past the flexible gasket. When the container cools, a vacuum will be formed in the container, automatically pulling the lid more tightly closed on the container base.

With radiation sterilizing, which does not rely on heat, the container lid is placed on the base in a lightly closed position, and the container is then subjected to a vacuum to withdraw air from the container past the flexible gasket. When pressure around the container is again allowed to increase, the lid will be tightly compressed on the base, since the gasket will prevent a pressure increase in the container. The container is then subjected to radiation, leaving the container contents sterilized and sealed in an essentially atmosphere free environment.

The container may be used for a wide variety of items in addition to surgical instruments. If it is used solely for towels, bandages, and other such somewhat bulky items, it may be convenient to invert the container so that the lid becomes the base, and not use the basket. The side walls of the inverted lid will hold items like towels more easily than will a flat base. The expandable chamber actuator would function in the same manner as described above. Once the container is closed, it could of course be returned to original position for storage and ease of handling. In the inverted position there would be no provision for drainage with the container illustrated; but there would be no drainage with towels. If desired the relief valve in the inverted lid may be modified to be open during the sterilizing phase and then automatically closed in response to temperature. Such a valve is described in the above application, Ser. No. 923,359. In addition to being a drain for condensate, a valve of this type would more importantly allow air to drain from the container as the steam or other sterilizing fluid is applied.

We claim:

1. Apparatus for containing items while being sterilized and stored comprising:
   means forming a container including means providing access to the container interior;
   support means holding said access means open;
   means attached to said support means forming an expandable chamber positioned so that expansion of said chamber will move said support means to release said access means and permit it to close; and
   a relief valve in said container for relieving a vacuum within said container to permit the access means to be opened, said relief valve including a filter therein arranged so that any air entering the container through the relief valve must pass through said filter;
   said relief valve comprises a resilient member having a tubular plug which is inserted into a hole in said container and includes an outer flange secured to said plug and sealed against the outer surface of said container, said tubular plug having a passage open at one end into the interior of said container and open at its other end through a port in the side wall of the said tubular plug adjacent said flange providing communication with the exterior of the chamber when the valve flange adjacent said port is partially pulled away from the container.

2. The apparatus of claim 1 wherein said filter comprises a rigid metal porous material positioned in the inner end of said plug so that all air entering the container must pass through said filter and the size of said filter is sufficient to help hold said plug in said access means with said flange held tightly against the container.

3. The apparatus of claim 1 wherein said valve flange includes an outwardly extending tab to be manually grasped for facilitating opening of the valve.

4. The apparatus of claim 3 wherein said valve flange includes an outwardly extending tab holder to which said tab may be attached for manually holding the flange in the valve open position.

5. The apparatus of claim 1 including an outwardly extending ring formed on said plug spaced from said flange and adjacent to an inner surface of said container to help hold the valve plug in said hole with said flange sealed against said container outer surface.

6. A container comprising:
a pair of members which cooperate to form an enclosure; and
a gasket positioned between the members, said gasket being formed of flexible resilient material and including a U-shaped portion which fits somewhat loosely over a peripheral flange formed on one of said members, said flange forming the outer most portion of said one member and a cylindrical portion attached to the open end of one leg of said U-shaped portion and surrounding the exterior of said one member adjacent said flange, said gasket further including an elongated annular flap which is secured to the open end of the other leg of said U-shaped portion and tapers to a thin feathered edge for mating with the other of said members to prevent fluid flow into the container when only the weight of the members compresses the gasket while still permitting flow out of the container when the pressure inside the container is greater than that outside the container, the junction between said annular flap and said other leg of the U-shaped portion being enlarged to form a bead to be compressed between the members to form a seal spaced inwardly from said feathered edge when pressure outside the container increases with respect to the container interior, said flap being constructed so that it is positioned to be compressed between said U-shaped portion and said other one of said members.

7. The apparatus of claim 6 wherein said members are a base and a lid and said flange is formed on said lid and the gasket is carried by the lid, and said flap is sufficiently flexible such that when one edge of the lid is raised from the base a few inches and then released to fall onto the base, a seal is formed by said feathered edge to prevent flow into the container.

8. Apparatus comprising a container having a wall with a hole extending therethrough, a resilient valve member having a tubular portion extending through said hole, said portion having a closed end and an open end and having a flange adjacent the closed end of the tubular portion, a passage through said tubular portion extending from the open end to a port in the sidewall of the tubular portion adjacent said flange, a filter positioned in the open end of said tubular portion causing that end of the tubular portion to bulge outwardly so that its outer diameter is larger than the hole in said wall, the filter being located such that the bulging end helps hold the valve member in said hole with said flange in engagement with the surface of the wall surrounding said hole thereby preventing fluid flow through the passage, said passage being openable by manually pulling a portion of the flange adjacent said port away from said wall to uncover the port and permit flow through the passage.

9. The apparatus of claim 8 including a tab attached to said flange for facilitating pulling the flange into position to uncover the port, and a tab holder attached to said flange for holding the tab in said position.

* * * * *